(12) United States Patent
Hosokai

(10) Patent No.: US 11,957,305 B2
(45) Date of Patent: Apr. 16, 2024

(54) ENDOSCOPE DISTAL END STRUCTURE AND ENDOSCOPE

(71) Applicant: OLYMPUS CORPORATION, Tokyo (JP)

(72) Inventor: Shigeru Hosokai, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 386 days.

(21) Appl. No.: 17/377,781

(22) Filed: Jul. 16, 2021

(65) Prior Publication Data

US 2021/0338059 A1 Nov. 4, 2021

Related U.S. Application Data

(63) Continuation of application No. PCT/JP2019/006153, filed on Feb. 19, 2019.

(51) Int. Cl.
*A61B 1/00* (2006.01)

(52) U.S. Cl.
CPC ...... *A61B 1/00096* (2013.01); *A61B 1/00018* (2013.01)

(58) Field of Classification Search
CPC ........... A61B 1/05; A61B 1/051; A61B 1/053; A61B 1/0096; A61B 1/0018;

(Continued)

(56) References Cited

U.S. PATENT DOCUMENTS

2007/0182842 A1   8/2007   Sonnenschein et al.
2009/0021618 A1*  1/2009   Schwarz .............. A61B 1/051
                                                        348/294

(Continued)

FOREIGN PATENT DOCUMENTS

CN   105282981 A   1/2016
CN   108778094 A   11/2018

(Continued)

OTHER PUBLICATIONS

International Search Report dated May 14, 2019 received in PCT/JP2019/006153.

(Continued)

*Primary Examiner* — Timothy J Neal
(74) *Attorney, Agent, or Firm* — Scully, Scott, Murphy & Presser, P.C.

(57) ABSTRACT

An endoscope distal end structure includes: an imaging unit; a signal cable; and a distal end frame including a housing portion, and a cable connection portion configured to connect the signal cable. The housing portion is a recess formed on a distal end side of the distal end frame. The housing portion includes a side surface and a bottom surface provided with a connection terminal. At least a part of the cable connection portion is provided with a cable connection electrode that connects a core wire of the signal cable on a distal end side from a bottom surface of the housing portion with reference to the optical axis direction of the imaging unit. The connection terminal and the cable connection electrode are connected by a wiring pattern formed in the housing portion, an outer periphery of the distal end frame, and the cable connection portion.

11 Claims, 16 Drawing Sheets

(58) Field of Classification Search
CPC ............ A61B 1/00114; A61B 1/00096; A61B 1/00018; A61B 1/00013; G02B 6/424; G02B 23/26
See application file for complete search history.

(56) References Cited

U.S. PATENT DOCUMENTS

| | | | |
|---|---|---|---|
| 2012/0292079 A1* | 11/2012 | Muramatsu | ............ H01B 7/048 174/113 R |
| 2017/0127915 A1* | 5/2017 | Viebach | ................. A61B 1/018 |
| 2019/0021582 A1 | 1/2019 | Shimizu | |

FOREIGN PATENT DOCUMENTS

| | | |
|---|---|---|
| JP | 09-061731 A | 3/1997 |
| JP | 11-305146 A | 11/1999 |
| JP | 2009-027709 A | 2/2009 |
| JP | 2017-505154 A | 2/2017 |

OTHER PUBLICATIONS

Chinese Office Action dated Jan. 19, 2024 received 201980088655.X.

* cited by examiner

ENDOSCOPE DISTAL END STRUCTURE AND ENDOSCOPE

This application is a continuation of International Application No. PCT/JP2019/006153, filed on Feb. 19, 2019, the entire contents of which are incorporated herein by reference.

BACKGROUND

The present disclosure relates to an endoscope distal end structure and an endoscope.

In the endoscope, a flexible insertion portion having an elongated shape with an imaging unit provided at the distal end is inserted into the subject such as a patient, so that image data inside the subject is acquired by the imaging unit disposed at a distal end portion, and the image data is transmitted to an external information processing apparatus by a signal cable. The imaging unit is held by a front frame body in order to fix a relative position with respect to another built-in component, and is protected by a cap or the like.

SUMMARY

According to one aspect of the present disclosure, there is provided an endoscope distal end structure including: an imaging unit configured to capture an image of a subject; a signal cable configured to transmit and receive a signal to and from the imaging unit; and a distal end frame that is a three-dimensional circuit component, the distal end frame including a housing portion having a side surface partially opened and configured to house the imaging unit, and a cable connection portion configured to connect the signal cable, wherein the housing portion is a recess formed on a distal end side of the distal end frame, the housing portion includes a bottom surface and a side surface, and the bottom surface is provided with a connection terminal for electrically connecting the imaging unit, at least a part of the cable connection portion is provided with a cable connection electrode that connects a core wire of the signal cable on a distal end side from a bottom surface of the housing portion with reference to the optical axis direction of the imaging unit, and the connection terminal and the cable connection electrode are connected by a wiring pattern formed in the housing portion, an outer periphery of the distal end frame, and the cable connection portion.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
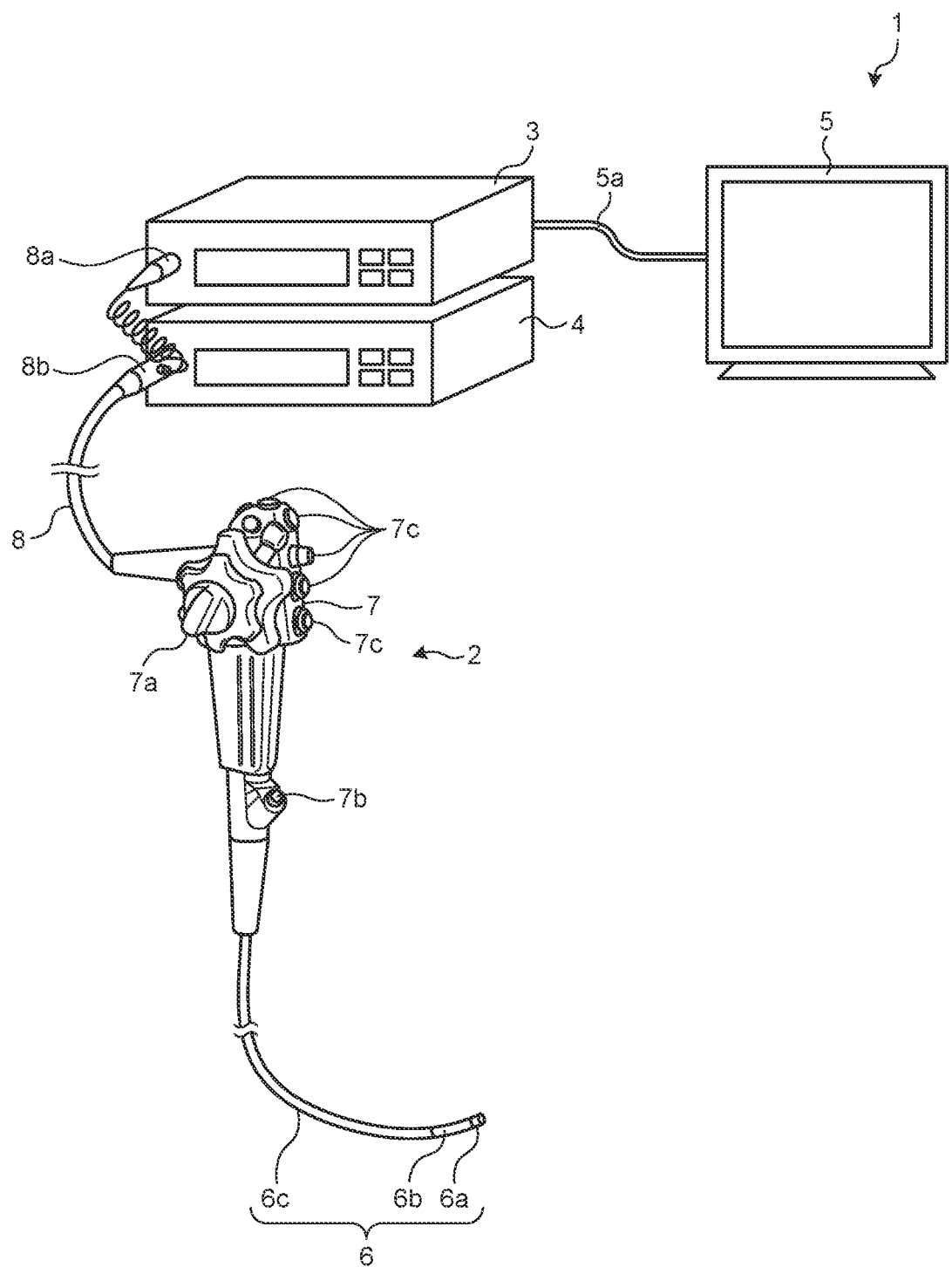
FIG. 1 is a diagram schematically illustrating an overall configuration of an endoscope system according to a first embodiment.

In the following description, an endoscope system including an endoscope distal end structure will be described as a mode (hereinafter, referred to as an "embodiment") for carrying out the present disclosure. Further, the present disclosure is not limited by the embodiment. Furthermore, in the description of the drawings, the same portions are denoted by the same reference numerals. Furthermore, it should be noted that the drawings are schematic, and the relationship between the thickness and the width of each member, the ratio of each member, and the like are different from reality. In addition, the drawings include portions having different dimensions and ratios.

First Embodiment

FIG. 1 is a diagram schematically illustrating an overall configuration of an endoscope system 1 according to a first embodiment. As illustrated in FIG. 1, the endoscope system 1 according to the first embodiment includes an endoscope 2 that is introduced into a subject and captures an image of an inside of the subject to generate an image signal of the inside of the subject, an information processing apparatus 3 that performs predetermined image processing on the image signal captured by the endoscope 2 and controls each unit of the endoscope system 1, a light source apparatus 4 that generates illumination light of the endoscope 2, and a display device 5 that displays an image of the image signal after the image processing by the information processing apparatus 3.

The endoscope 2 includes an insertion portion 6 to be inserted into the subject, an operating unit 7 that is a proximal end portion side of the insertion portion 6 and is gripped by an operator, and a flexible universal cord 8 extending from the operating unit 7.

The insertion portion 6 is realized by using a light guide cable, an electric cable, an optical fiber, and the like. The insertion portion 6 includes a distal end portion 6a incorporating an imaging unit to be described later, a bendable bending portion 6b including a plurality of bending pieces, and a flexible tube portion 6c having flexibility provided on the proximal end portion side of the bending portion 6b. The distal end portion 6a is provided with an aperture communicating the light guide cable for illuminating the inside of the subject, the imaging unit for capturing the inside of the subject, and a treatment tool channel.

The operating unit 7 includes a bending knob 7a that bends the bending portion 6b in the vertical direction and the horizontal direction, a treatment tool insertion portion 7b in which a treatment tool such as a biological forceps or a laser scalpel is inserted into a body cavity of the subject, and a plurality of switch units 7c that operate peripheral equipment such as the information processing apparatus 3, the light source apparatus 4, an air supply device, a water supply device, and a gas supply device. The treatment tool inserted from the treatment tool insertion portion 7b passes through a treatment tool channel provided inside and comes out from the aperture at a distal end of the insertion portion 6.

The universal cord 8 is configured using the light guide cable, the electric cable, and the like. The universal cord 8 is branched at a proximal end, and one branched end portion is a connector 8a and the other proximal end is a connector 8b. The connector 8a is attachable to and detachable from a connector of the information processing apparatus 3. The connector 8b is attachable to and detachable from the light source apparatus 4. The universal cord 8 propagates the illumination light emitted from the light source apparatus 4 to the distal end portion 6a via the connector 8b and the light guide cable. In addition, the universal cord 8 transmits the image signal captured by the imaging unit to be described later to the information processing apparatus 3 via the cable and the connector 8a.

The information processing apparatus 3 performs the predetermined image processing on the image signal output from the connector 8a and controls the entire endoscope system 1.

The light source apparatus 4 is configured using a light source that emits light, a condenser lens, and the like. Under control of the information processing apparatus 3, the light source apparatus 4 emits light from the light source and supplies the light as the illumination light for the inside of the subject which is a subject to be captured, to the endoscope 2 connected via the connector 8b and the light guide cable of the universal cord 8.

The display device 5 is configured using a display or the like using liquid crystal or organic electro luminescence (EL). The display device 5 displays various types of information including the image subjected to the predetermined image processing by the information processing apparatus 3 via a video cable 5a. As a result, the operator may observe a desired position in the subject and determine the property by operating the endoscope 2 while viewing the image (in-vivo image) displayed by the display device 5.

Figure 2:
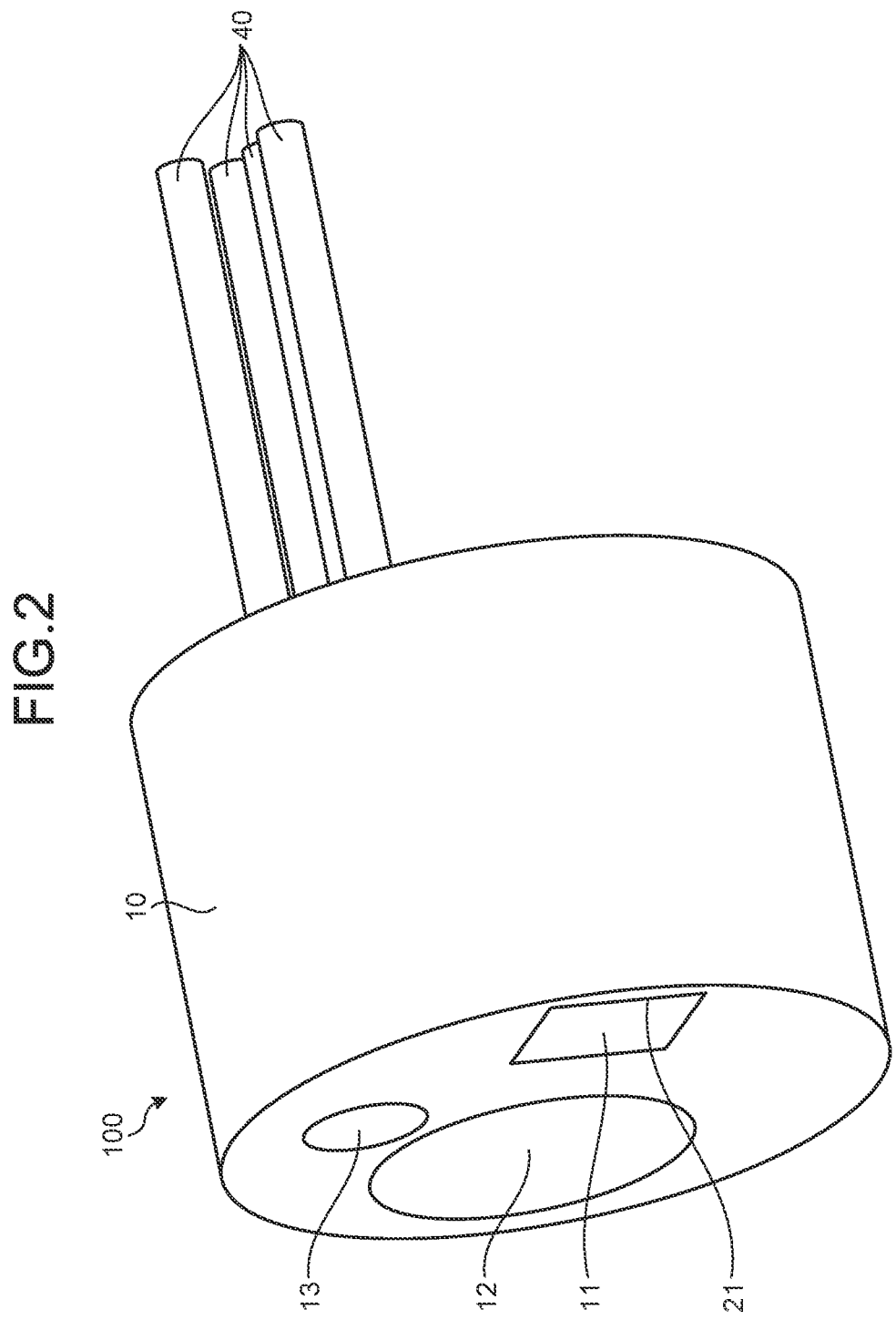
FIG. 2 is a perspective view of an endoscope distal end structure disposed at a distal end portion of the endoscope illustrated in FIG. 1.
Figure 3:
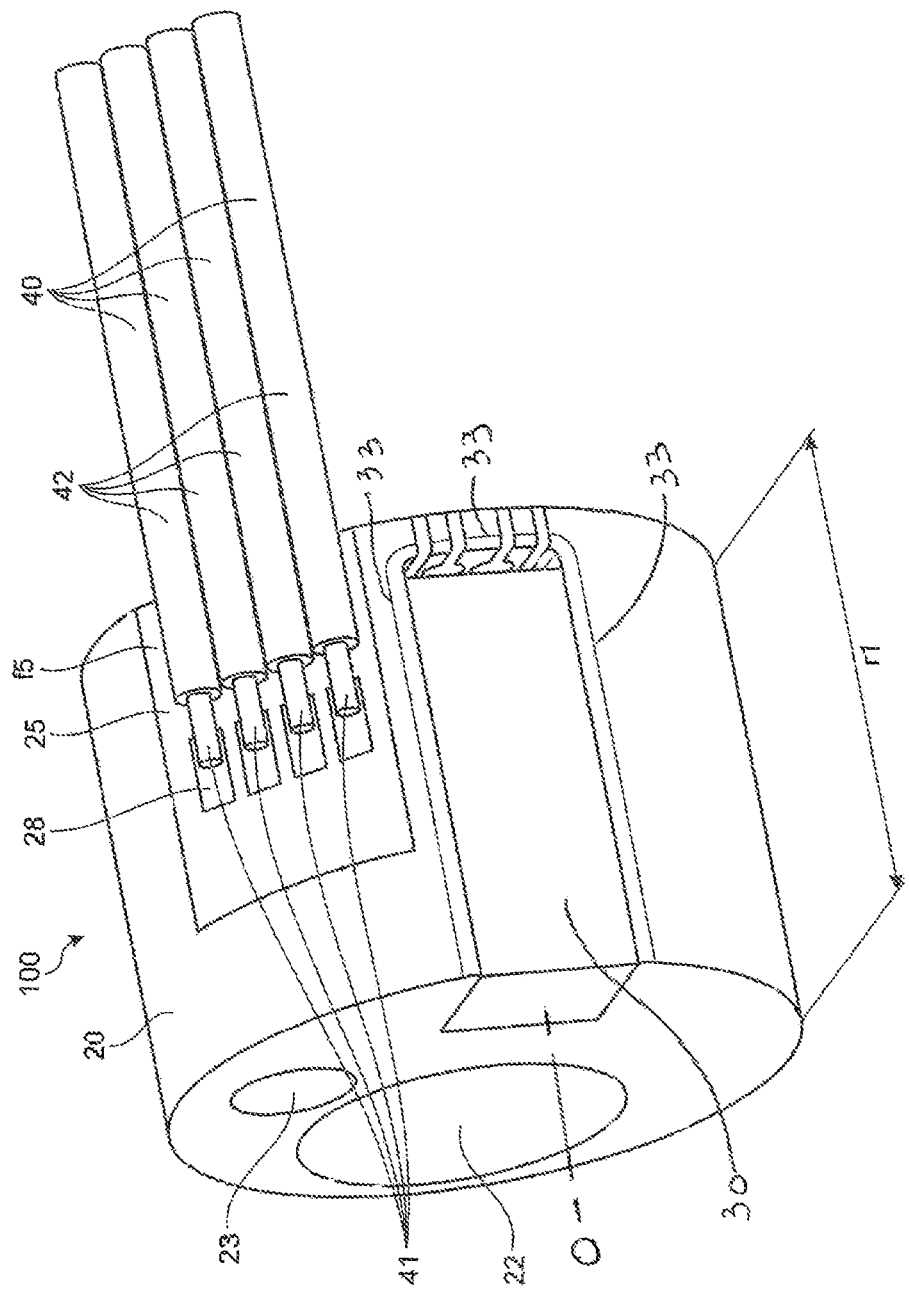
FIG. 3 is a perspective view of a state in which an outer frame is removed from the endoscope distal end structure of FIG. 2.
Figure 4:
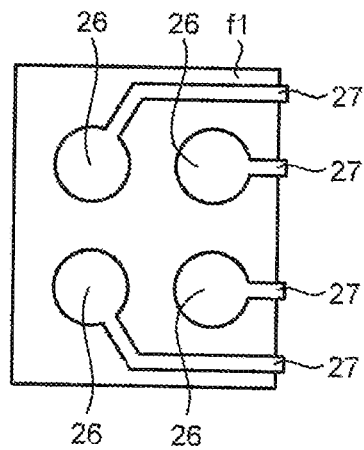
FIG. 4 is a view illustrating a structure of a housing portion of a distal end frame in FIG. 3.
Figure 5:
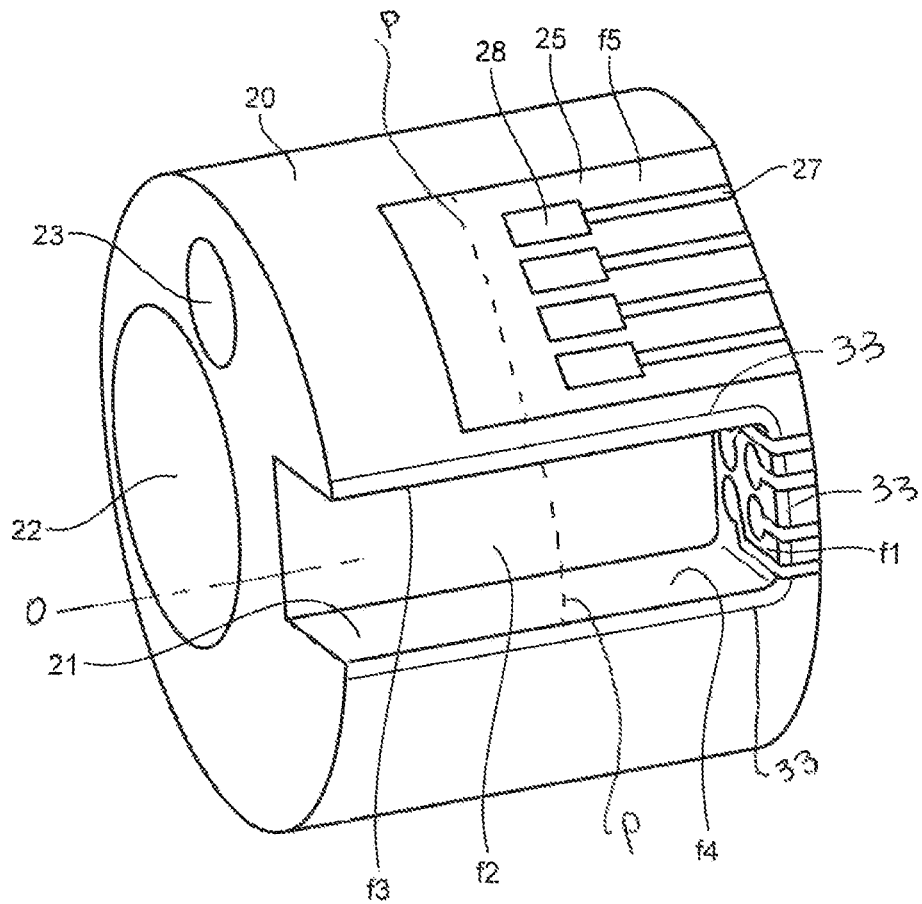
FIG. 5 is a perspective view of the distal end frame used for the endoscope distal end structure of FIG. 3.
Figure 6:
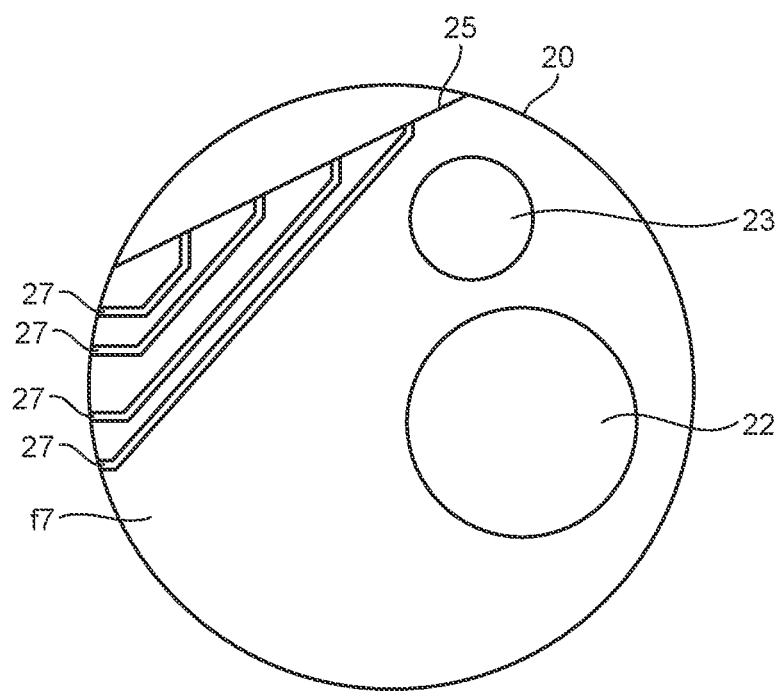
FIG. 6 is a view of the distal end frame of FIG. 5 as viewed from a proximal end side.

Next, an endoscope distal end structure 100 used in the endoscope system. 1 will be described in detail. FIG. 2 is a perspective view of the endoscope distal end structure 100 disposed at a distal end portion of the endoscope 2 illustrated in FIG. 1, FIG. 3 is a perspective view of a state in which an outer frame 10 is removed from the endoscope distal end structure 100 of FIG. 2, FIG. 4 is a view illustrating a structure of a housing portion 21 of a distal end frame 20 of FIG. 3, FIG. 5 is a perspective view of the distal end frame 20 used for the endoscope distal end structure 100 of FIG. 3, and FIG. 6 is a view of the distal end frame 20 of FIG. 3 as viewed from a proximal end side. In FIGS. 2 and 3, illustration of the light guide and the channel is omitted. Note that in the present specification, the distal end portion 6a side of the endoscope 2 is referred to as a distal end side, and a side from which a signal cable 40 extends is referred to as the proximal end side.

The endoscope distal end structure 100 includes an imaging unit 30 that captures the subject to be captured, the signal cable 40 that transmits and receives signals to and from the imaging unit 30, the distal end frame 20 that is a molded interconnect device having a substantially columnar outer shape, and the cuter frame 10 that covers a periphery of the distal end frame 20.

The imaging unit 30 includes an optical unit (not illustrated) that forms an image of the subject to be captured, and an imaging element (not illustrated) that photoelectrically converts the image of the subject to be captured formed by the optical unit and generates the image signal, the imaging element includes a CCD, a CMOS, or the like, and a light receiving unit is covered with a cover glass.

The distal end frame 20 is the molded interconnect device (MID) manufactured by injection molding, cutting, or the like and formed with three-dimensional wiring. In the first embodiment, since the MID is used as the distal end frame 20, it is possible to simply and inexpensively manufacture even a complicated structure after forming circuit wiring at an arbitrary position. Examples of material of the distal end frame 20 include liquid crystal polymer, polyamide, and polycarbonate. By using the molded interconnect device as the distal end frame 20, the endoscope distal end structure 100 may be easily and inexpensively manufactured. Note that the distal end frame 20 of the first embodiment has a columnar shape, but is not limited thereto. As an outer diameter of the distal end frame 20, a shape applicable to the endoscope distal end structure may be adopted, such as a polygonal columnar shape, a columnar shape having a shape in which a part of a circular outer shape of a bottom surface is cut away, and a columnar shape having a shape in which a part of the bottom surface projects from the circular outer shape.

The distal end frame 20 includes the housing portion 21 that houses the imaging unit 30, a channel insertion hole 22 through which a channel tube is inserted, a light guide insertion hole 23 through which the light guide is inserted, and a cable connection portion 25 that connects the signal cable 40. The channel insertion hole 22 and the light guide insertion hole 23 are through-holes penetrating from the distal end side to the proximal end side of the distal end frame 20, and are arranged in parallel with an optical axis O direction of the imaging unit 30. In the first embodiment, since the signal cable 40, the channel tube, and the light guide have flexibility, a length r1 from the distal end side to the proximal end side of the distal end frame 20 is a part of a hard portion of the endoscope 2.

The housing portion 21 is a recess formed on the distal end side of distal end frame 20, and a part of a surface on the distal end side of distal end frame 20 and a part of a side surface are opened. As illustrated in FIG. 5, the housing portion 21 includes a bottom surface f1 perpendicular to the optical axis O direction of the imaging unit 30 and side surfaces f2, f3, and f4 parallel to the optical axis O direction of the imaging unit 30. A connection terminal 26 for electrically connecting the imaging unit 30 is formed on the bottom surface f1. A connection land (not illustrated) of the imaging unit 30 is electrically and mechanically connected to the connection terminal 26 by a bump 31 (see FIG. 4) made of solder or the like. The connection terminal 26 includes a power terminal required to drive the imaging unit 30, a ground terminal, a video output terminal, a clock terminal, a communication signal terminal, and the like. Note that, although not illustrated in FIGS. 3 and 4, a gap between the imaging unit 30 and the housing portion 21 (including a connection portion between the imaging unit 30 and the connection terminal 26) and a side surface portion not in contact with the housing portion 21 of the imaging unit 30 are covered with a resin such as an underfill.

The cable connection portion 25 includes a plane f5 in which the proximal end side of the distal end frame 20 is cut out. As illustrated in FIG. 5, when viewed in a front-rear direction with reference to the optical axis O direction of the imaging unit 30, a cable connection electrode 28 that connects a core wire 41 of the signal cable 40 is formed on the distal end side from the bottom surface f1 of the housing portion 21. In the signal cable 40, an insulating jacket 42 on the distal end side is removed to expose the core wire 41, and the exposed core wire 41 is connected to the cable connection electrode 28 by a conductive material such as solder (not illustrated).

A wiring pattern 27 for connecting the connection terminal 26 and the cable connection electrode 28 is formed in the housing portion 21, a part of an outer periphery of the distal end frame 20, and the cable connection portion 25. In the first embodiment, the wiring pattern 27 is wired from the bottom surface f1 of the housing portion 21, on the outer periphery of the distal end frame 20 (a side surface of the distal end frame 20 parallel to the optical axis O direction of the imaging unit 30 between the housing portion 21 and a proximal end surface f7), the proximal end surface f7, and the plane f5 of the cable connection portion 25.

Figure 7:
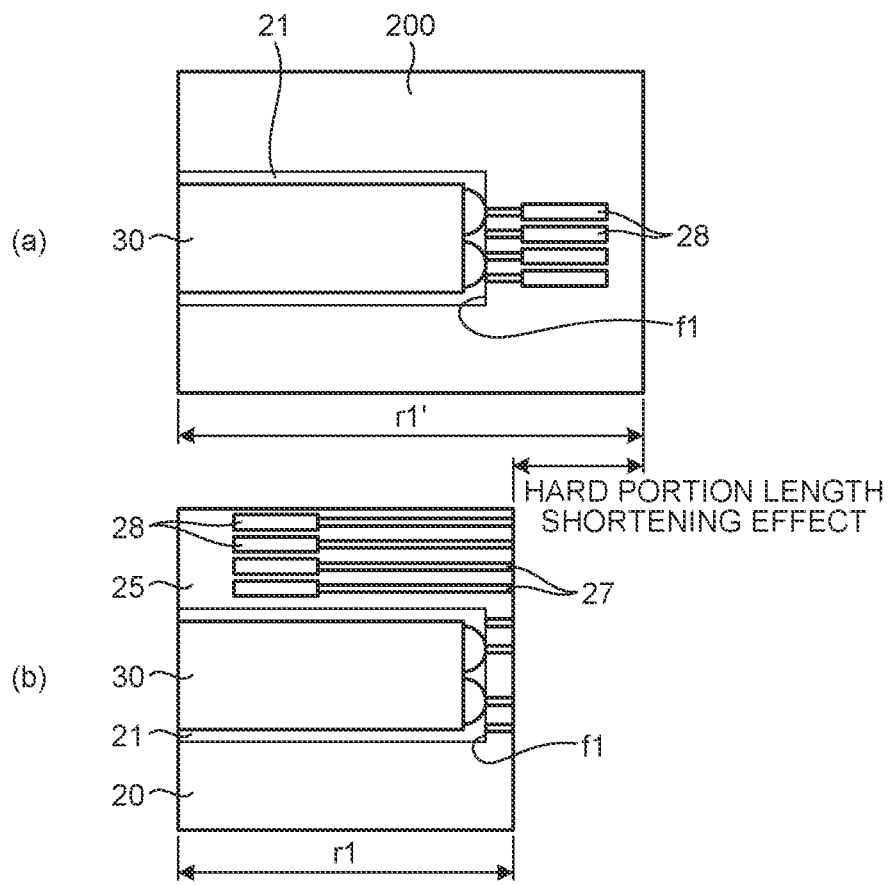
FIG. 7 is a side view illustrating an arrangement position of a cable connection electrode of the distal end frame according to the first embodiment.

FIG. 7 is a side view for explaining an arrangement position of the cable connection electrode 28 of the distal end frame 20 according to the first embodiment, a part (a) of FIG. 7 illustrates a conventional technique, and a part (b) of FIG. 7 illustrates the distal end frame 20 according to the first embodiment. In a distal end frame 200 of the conventional technique, since the cable connection electrode 28 is disposed on the proximal end side from the bottom surface f1 of the housing portion 21 of the imaging unit 30, a length r1' of the distal end frame 200 in the optical axis O direction is longer by a length of the cable connection electrode 28. On the other hand, in the distal end frame 20 of the first embodiment, since the cable connection electrode 28 is formed on the distal end side from the bottom surface f1 of the housing portion 21, the length r1 of the distal end frame in the optical axis O direction may be reduced.

Corners of portions where the wiring pattern 27 is formed, that is, a corner between the bottom surface f1 of the housing portion 21 and the outer periphery (side surface) of the distal end frame 20, a part of a corner between the outer periphery (side surface) of the distal end frame 20 and the proximal end surface f7, and a corner between the proximal end surface f7 and the cable connection portion 25 have a chamfer 33. By chamfering the corners, it is possible to prevent degradation of quality of electric signals transmitted through the wiring pattern 27. The chamfering is preferably R-chamfering, but may be C-chamfering.

In the endoscope distal end structure 100, in a state where the imaging unit 30 is housed in the distal end frame 20 and the signal cable 40 is connected to the cable connection portion 25, the imaging unit 30 and the signal cable 40 are located in a projection plane P in the optical axis O direction of a circumscribed circle of a distal end surface of the distal end frame 20. Thus, it is possible to suppress an increase in diameter of the endoscope distal end structure 100.

The outer frame 10 has a hollow cylindrical shape with the proximal end side opened, and a surface on the distal end side is provided with an aperture 11, an aperture 12, and an aperture 13 at positions overlapping the housing portion 21, the channel insertion hole 22, and the light guide insertion hole 23.

In the first embodiment, by forming the cable connection electrode 28 on the distal end side from the bottom surface f1 of the housing portion 21, it is possible to shorten the hard portion of the endoscope 2. In addition, since the imaging unit 30 and the signal cable 40 are located in the projection plane P of the distal end frame 20 in the optical axis O direction, it is possible to suppress the increase in the diameter of the endoscope distal end structure 100.

In the endoscope distal end structure 100 of the first embodiment, the distal end frame 20 has the channel insertion hole 22 and the light guide insertion hole 23, but even when it does not have the channel insertion hole 22, it is possible to reduce a diameter and a length of the hard portion of the endoscope.

Second Embodiment

Figure 8:
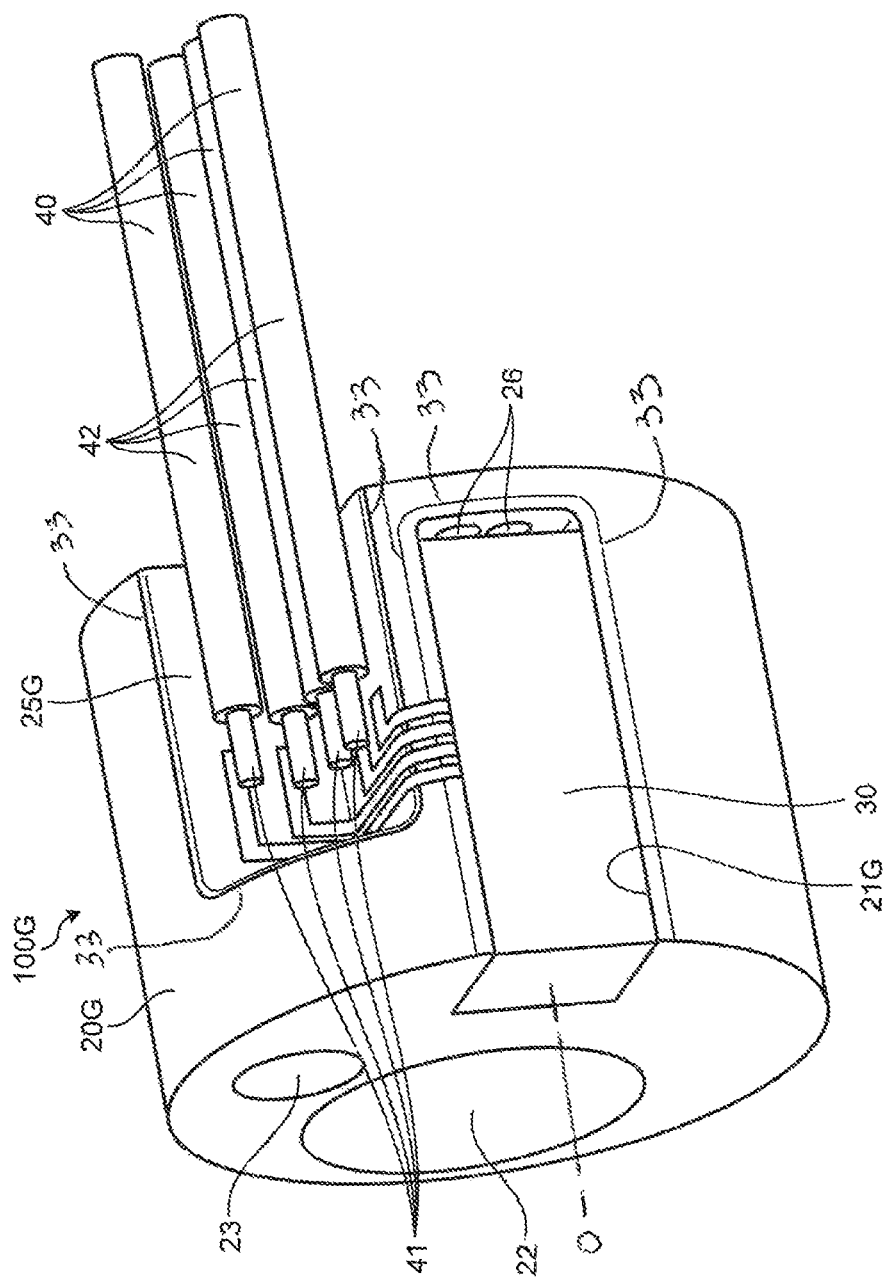
FIG. 8 is a perspective view of the endoscope distal end structure according to a second embodiment.
Figure 9:
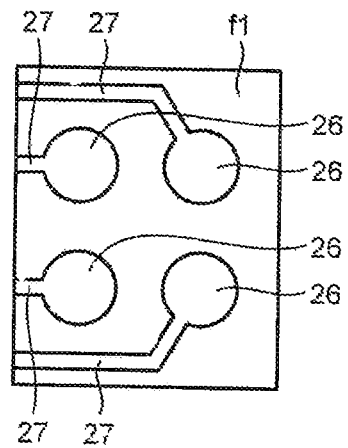
FIG. 9 is a perspective view of the state in which the outer frame is removed from the endoscope distal end structure of FIG. 8.
Figure 10:
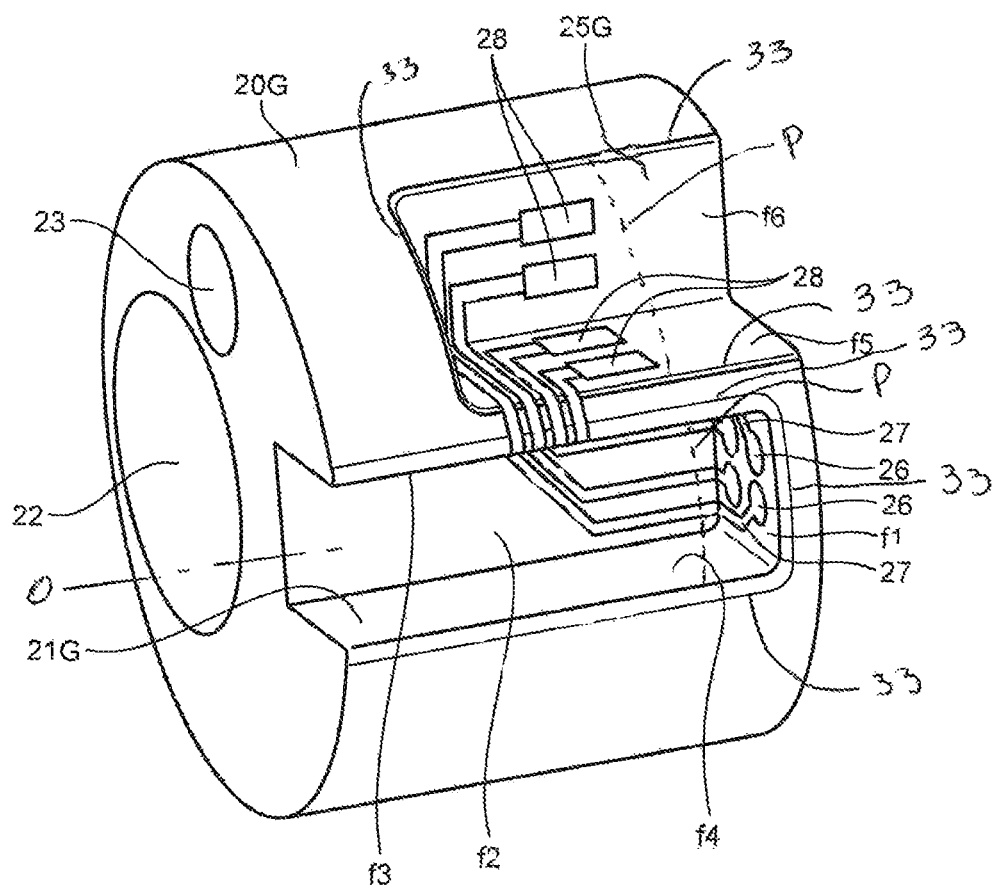
FIG. 10 is a view illustrating the structure of the housing portion of the distal end frame in FIG. 8.

FIG. 8 is a perspective view of an endoscope distal end structure 100G according to a second embodiment, FIG. 9 is a view illustrating a structure of a housing portion 21G of a distal end frame 20G of FIG. 8, and FIG. 10 is a perspective view of the distal end frame 20G used in the endoscope distal end structure 1000 of FIG. 3. Note that in FIG. 8, illustration of the outer frame 10, the light guide, and the channel is omitted.

The distal end frame 20G includes the housing portion 21G that houses the imaging unit 30, the channel insertion hole 22 through which the channel tube is inserted, the light guide insertion hole 23 through which the light guide is inserted, and a cable connection portion 25G that connects the signal cable 40.

The cable connection portion 25G is formed by cutting out the proximal end side of the distal end frame 20G, and includes planes f5 and f6. The wiring pattern 27 for connecting the connection terminal 26 and the cable connection electrode 26 is formed in the housing portion 21, a part of the outer periphery (side surface) of the distal end frame 20G, and the cable connection portion 25G. In the second embodiment, the wiring pattern 27 is wired from the bottom surface f1 of the housing portion 21G through the side surfaces f2 and f3, on the outer periphery of the distal end frame 20G (between the housing portion 21 and the cable connection portion 25G), and on the planes f5 and f6 of the cable connection portion 25G. The wiring pattern 27 may be wired from the bottom surface f1 to the side surface f3 without passing through the side surface f2 of the housing portion 21.

In addition, corners of the housing portion 21G in which the wiring pattern 27 is formed, of a part of the outer periphery (side surface) of the distal end frame 20G, and of the cable connection portion 25G, that is, a corner between the bottom surface f1 and the side surface f2 of the housing portion 21G, a corner between the side surface f2 and the side surface f3, a corner between the side surface f3 and the outer periphery (side surface) of the distal end frame 20G, a corner between the outer periphery (side surface) of the distal end frame 20G and the plane f5 of the cable connection portion 25G, and a corner between the plane f5 and the plane f6 have a chamfer 33. By chamfering the corners, it is possible to prevent degradation of quality of electric signals transmitted through the wiring pattern 27.

In the endoscope distal end structure 100G, in the state where the imaging unit 30 is housed in the distal end frame 20G and the signal cable 40 is connected to the cable connection portion 25G, the imaging unit 30 and the signal cable 40 are located in the projection plane P of the circumscribed circle of the distal end surface in the optical axis O direction of the distal end frame 20G. Thus, it is possible to suppress the increase in the diameter of the endoscope distal end structure 100G.

In the second embodiment, by forming the cable connection electrode 28 on the distal end side from the bottom surface f1 of the housing portion 21G, it is possible to shorten the hard portion of the endoscope 2. In addition, since the imaging unit 30 and the signal cable 40 are located in the projection plane P of the distal end frame 20G in the optical axis O direction, it is possible to suppress the increase in the diameter of the endoscope distal end structure 100G.

Figure 11:
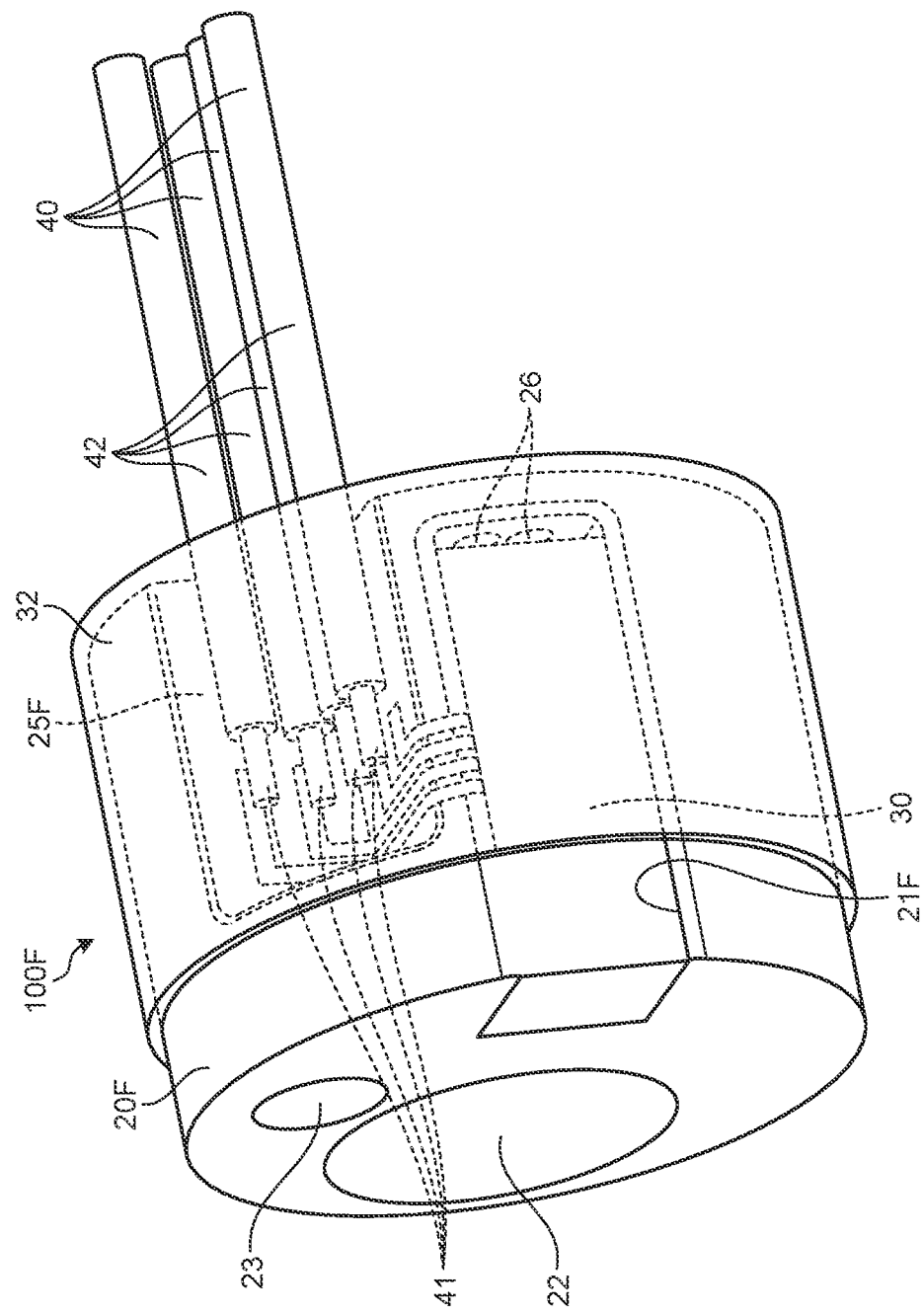
FIG. 11 is a perspective view of the endoscope distal end structure according to a modification of the second embodiment.

Note that in the second embodiment, an entire distal end frame 20G is covered with the outer frame, but the entire distal end frame is not necessarily covered. FIG. 11 is a perspective view of an endoscope distal end structure 100F according to a modification of the second embodiment. In the endoscope distal end structure 100F, the proximal end side of a distal end frame 20S on which a cable connection portion 25F is formed is covered with an outer frame 32. By covering the connection portion between the signal cable 40 and the cable connection electrode 28 and the connection portion between the imaging unit 30 and the connection terminal 26 with the outer frame 32, it is possible to prevent the wiring pattern 27 from being exposed and to reduce the diameter of the distal end portion.

Third Embodiment

Figure 12:
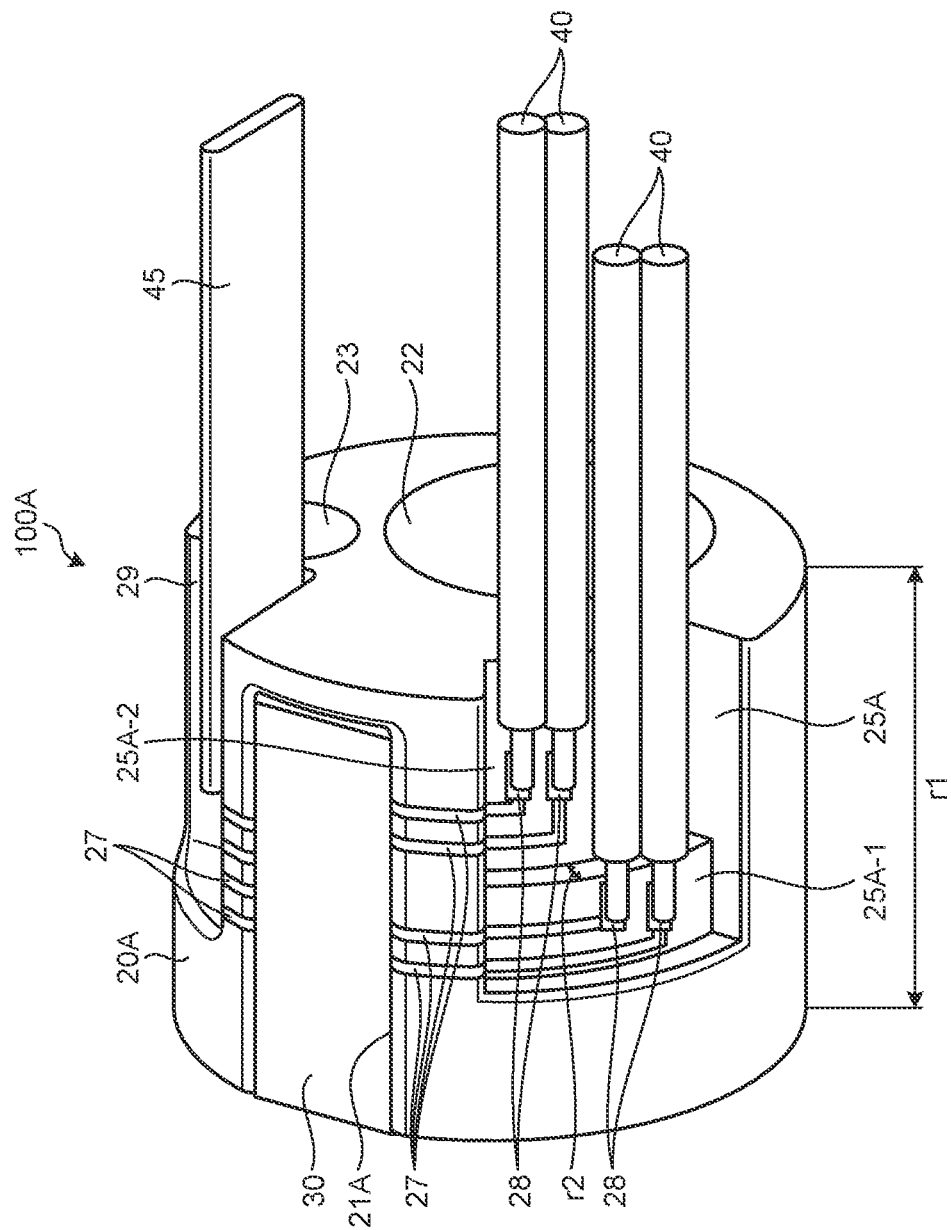
FIG. 12 is a perspective view of the endoscope distal end structure according to a third embodiment.
Figure 13:
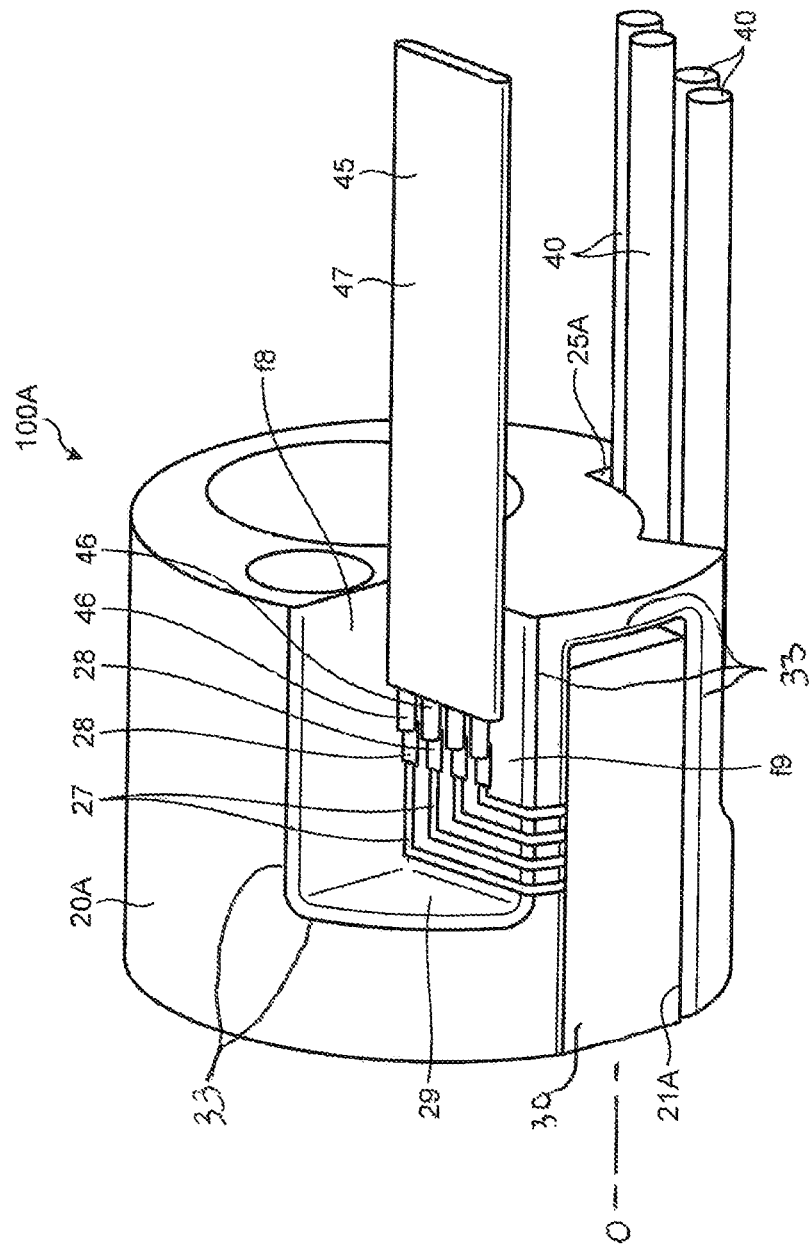
FIG. 13 is a perspective view of the endoscope distal end structure of FIG. 12 from another direction.

In a third embodiment, the distal end frame 20A includes a flat cable connection portion 29 that connects a flat cable 45 in addition to a cable connection portion 25A. FIG. 12 is a perspective view of an endoscope distal end structure 100A according to the third embodiment, and FIG. 13 is a perspective view of the endoscope distal end structure 100A of FIG. 12 from another direction. In FIGS. 12 and 13, the illustration of the outer frame, the light guide, and the channel is omitted.

The cable connection portion 25A includes a circumferential surface 25A-1 and a circumferential surface 25A-2 concentric with the outer periphery of the distal end frame 20A. The circumferential surface 25A-1 and the circumferential surface 25A-2 are formed such that the proximal end side, that is, a diameter of the circumferential surface 25A-2 is shorter than that of the circumferential surface 25A-1.

In FIG. 12, two signal cables 40 are connected to each of the circumferential surface 25A-1 and the circumferential surface 25A-2, however, by setting a step r2 between the circumferential surface 25A-1 and the circumferential surface 25A-2 to be equal to or larger than a diameter of the signal cable 40, more signal cables 40 may be connected.

In the flat cable 45, a plurality of core wires 46 arranged in a strip shape are covered with an insulating coating 47, and the core wires 46 are exposed at an end portion of the flat cable 45.

The flat cable connection portion 29 is formed by cutting out the proximal end side of the distal end frame 20, and includes planes f8 and f9. The cable connection portion 25A and the flat cable connection portion 29 are provided to sandwich a cross-section including a central axis of the channel insertion hole 22 and an optical axis O of the imaging unit 30. When viewed in the front-rear direction with reference to the optical axis O direction of the imaging unit 30, the cable connection electrode 28 that connects the core wire 41 of the signal cable 40 and the core wire 46 of the flat cable 45 is formed on the distal end side from the bottom surface f1 of the housing portion 21 as illustrated in FIGS. 12 and 13. By forming the cable connection electrode 28 on the distal end side from the bottom surface f1 of a housing portion 21A, the length r1 of the distal end frame 20A in the optical axis O direction may be reduced.

In addition, the corners of the housing portion 21A in which the wiring pattern 27 is formed, of a part of the outer periphery (side surface) of the distal end frame 20A, and of the cable connection portion 25A, and a corner of the flat cable connection portion 29, that is, the corner between the bottom surface f1 and the side surface f2 of the housing portion 21, a corner between the side surface f2 and the side surface f4, a corner between the side surface f4 and the outer periphery (side surface) of the distal end frame 20A, a corner between the outer periphery (side surface) of the distal end frame 20A and the cable connection portion 25A, the corner between the side surface f2 and the side surface f3, the corner between the side surface f3 and the outer periphery (side surface) of the distal end frame 20A, and a corner between the outer periphery (side surface) of the distal end frame 20A and the flat cable connection portion 29 have a chamfer 33. By chamfering the corners, it is possible to prevent degradation of quality of electric signals transmitted through the wiring pattern 27.

In the third embodiment, since the flat cable connection portion 29 is provided in addition to the cable connection portion 25A, more signals may be transmitted and received to and from the signal cable 40 and the flat cable 45. Further, in mounting of another pin on the distal end frame 20A of the flat cable 45, a process of mounting may be simplified. Note that in a case where a flexible printed circuit board is used instead of the flat cable, a similar effect may be obtained.

In the third embodiment described above, the cable connection portion 25A includes the circumferential surface 25A-1 and the circumferential surface 25A-2, but may include one circumferential surface. In addition, two cable connection portions 25A may be arranged or two flat cable connection portions 29 may be arranged to sandwich the cross-section including the central axis of the channel insertion hole 22 and the optical axis O of the imaging unit 30.

Furthermore, in the third embodiment, the distal end frame 20A has the channel insertion hole 22 and the light guide insertion hole 23, but when it does not have the channel insertion hole 22, the cable connection portion 25A and the flat cable connection portion 29 only need to be provided to sandwich a cross-section including the central axis of the light guide insertion hole 23 and the optical axis O of the imaging unit 30.

Fourth Embodiment

Figure 14:
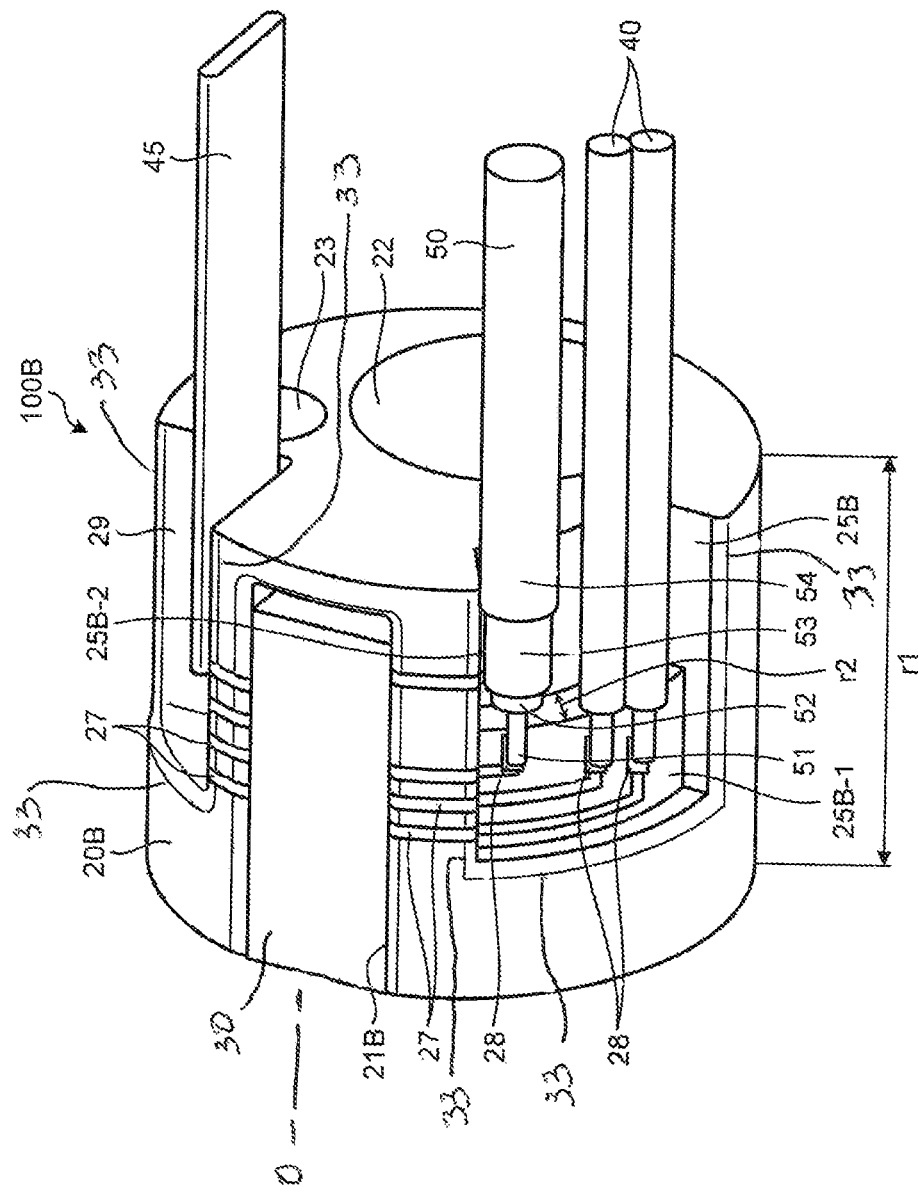
FIG. 14 is a perspective view of the endoscope distal end structure according to a fourth embodiment.
Figure 15:
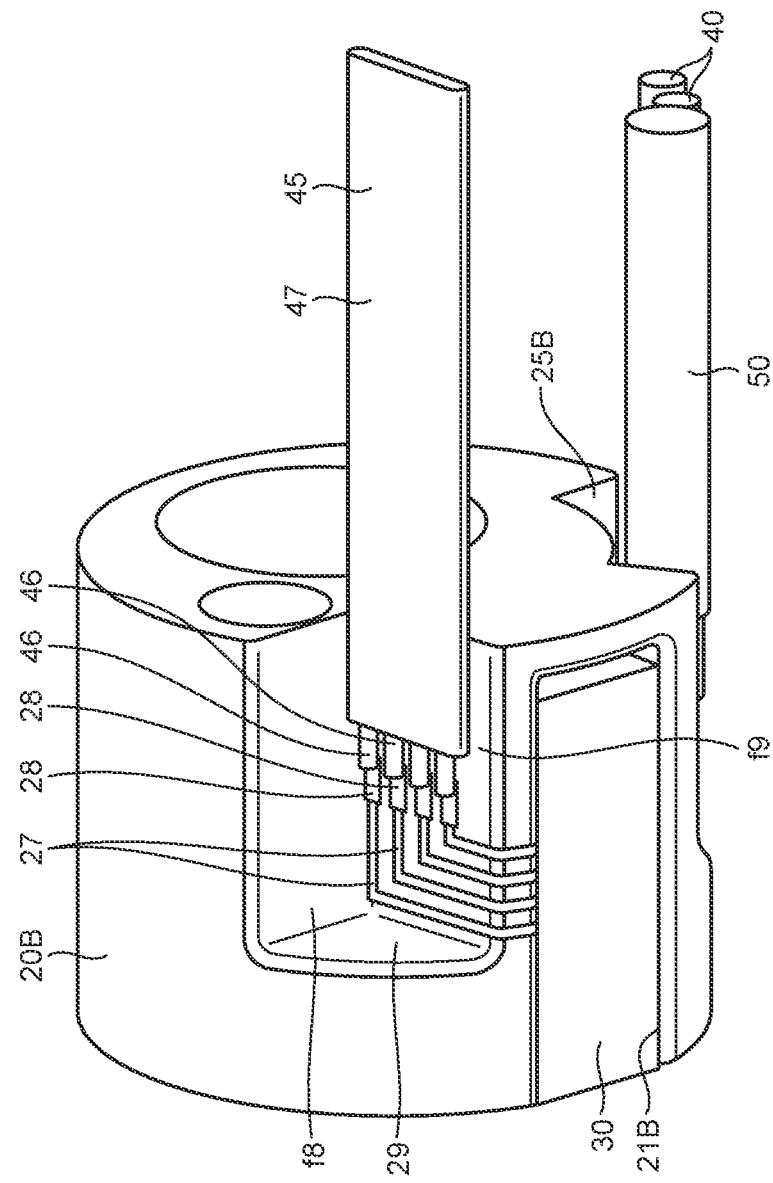
FIG. 15 is a perspective view of the endoscope distal end structure of FIG. 14 from another direction.

In a fourth embodiment, a distal end frame 20B connects a coaxial cable 50 to a cable connection portion 25B. FIG. 14 is a perspective view of an endoscope distal end structure 100B according to the fourth embodiment, and FIG. 15 its a perspective view of the endoscope distal end structure 100B of FIG. 14 from another direction. In FIGS. 14 and 15, the illustration of the outer frame, the light guide, and the channel is omitted.

The cable connection portion 25B includes a circumferential surface 25B-1 and a circumferential surface 25B-2 concentric with the outer periphery of the distal end frame 20B. The circumferential surface 25B-1 and the circumferential surface 25B-2 are formed such that the proximal end side, that is, the diameter of the circumferential surface 25B-2 is shorter than that of the circumferential surface 25B-1. Note that in the fourth embodiment, the cable connection portion 25B includes the circumferential surfaces 25B-1 and 25B-2, but may include a plurality of steps of planes (a stepped shape in which the proximal end side approaches the center).

The coaxial cable 50 includes a core wire 51, an inner insulator 52 covering the core wire, a shield 53 covering the inner insulator 52, and an outer insulator 54 covering the shield 53, and the outer insulator 54, the shield 53, and the inner insulator 52 are removed such that the core wire 51, the inner insulator 52, and the shield 53 are respectively exposed at end portions thereof.

The cable connection electrodes 28 that connect the core wire 41 of the signal cable 40 and the core wire 51 of the coaxial cable 50 are formed on the circumferential surface 25B-1 of the cable connection portion 25B. A cable connection electrode for connecting the shield 53 of the coaxial cable 50 is formed on the circumferential surface 25B-2. By connecting the core wire 51 and the shield 53 of the coaxial cable 50 respectively to the circumferential surface 25B-1 and the circumferential surface 25B-2 having the step r2, it is possible to easily connect the coaxial cable 50 and to reduce possibility of disconnection due to breakage or the like of the core wire 51.

In FIG. 14, the two signal cables 40 and the core wire of the coaxial cable 50 are connected to the circumferential surface 25B-1, and the shield 53 is connected to the circumferential surface 25B-2, however, by setting the step r2 between the circumferential surface 25B-1 and the circumferential surface 25B-2 to be equal to or larger than the diameter of the signal cable 40, the signal cable 40 may also be connected to the circumferential surface 25B-2.

The cable connection portion 25B and the flat cable connection portion 29 are provided to sandwich the cross-section including the central axis of the channel insertion hole 22 and the optical axis O of the imaging unit 30. When viewed in the front-rear direction with reference to the optical axis O direction of the imaging unit 30, the core wire 41 of the signal cable 40, the core wire 51 of the coaxial cable 50, the shield 53, and the cable connection electrode 28 connecting the core wire 46 of the flat cable 45 are formed on the distal end side from the bottom surface f1 of the housing portion 21B as illustrated in FIGS. 14 and 15. By forming the cable connection electrode 28 on the distal end side from the bottom surface f1 of the housing portion 21B, the length r1 of the distal end frame 20B in the optical axis O direction may be reduced.

In addition, the corners of the housing portion 21B in which the wiring pattern 27 is formed, of a part of the outer periphery (side surface) of the distal end frame 20B, and of the cable connection portion 25B, and the corner of the flat cable connection portion 29, that is, the corner between the bottom surface f1 and the side surface f2 of the housing portion 21, the corner between the side surface f2 and the side surface f4, the corner between the side surface f4 and the outer periphery (side surface) of the distal end frame 20B, the corner between the outer periphery (side surface) of the distal end frame 20B and the cable connection portion 25B, the corner between the side surface f2 and the side surface f3, the corner between the side surface f3 and the outer periphery (side surface) of the distal end frame 20B, and the corner between the outer periphery (side surface) of the distal end frame 20B and the flat cable connection portion 29 have a chamfer 33. By chamfering the corners, it is possible to prevent degradation of quality of electric signals transmitted through the wiring pattern 27.

Fifth Embodiment

Figure 16:
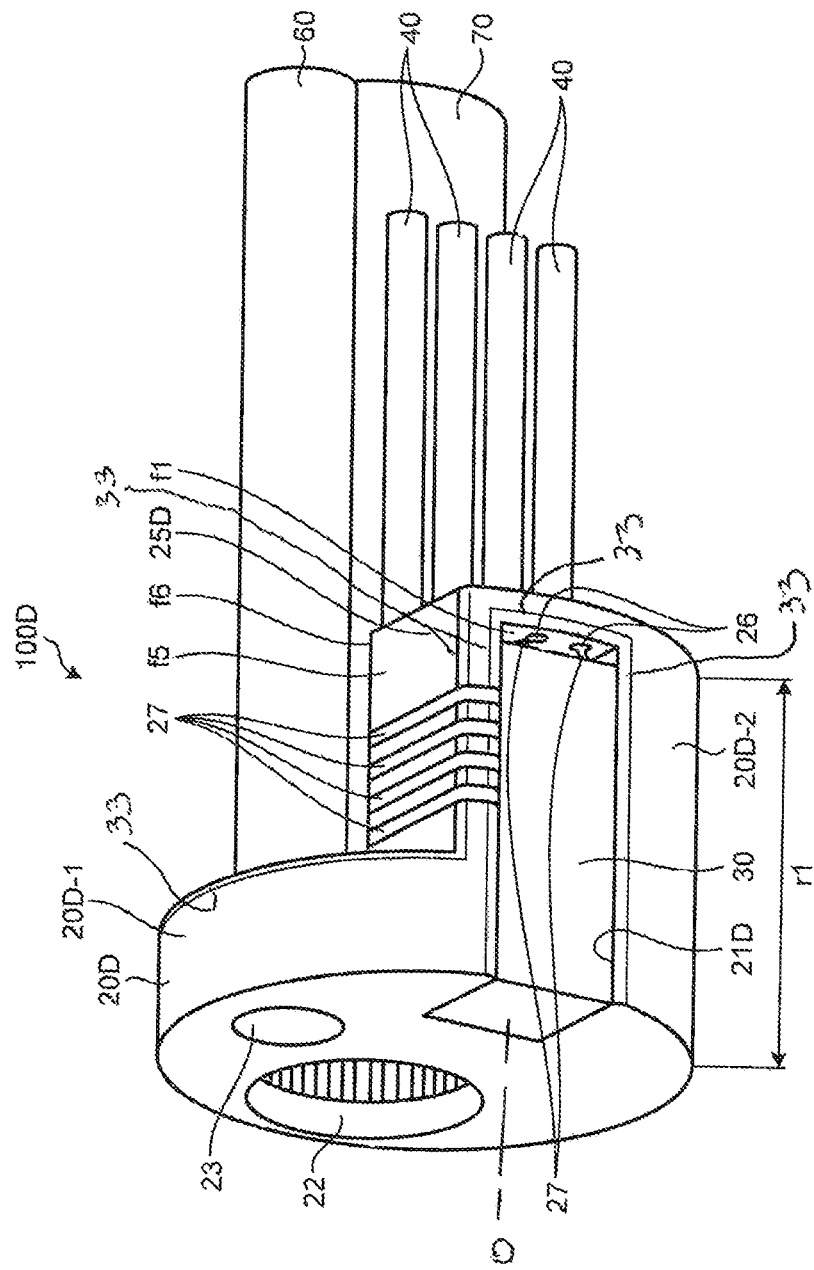
FIG. 16 is a perspective view of the endoscope distal end structure according to a fifth embodiment.
Figure 17:
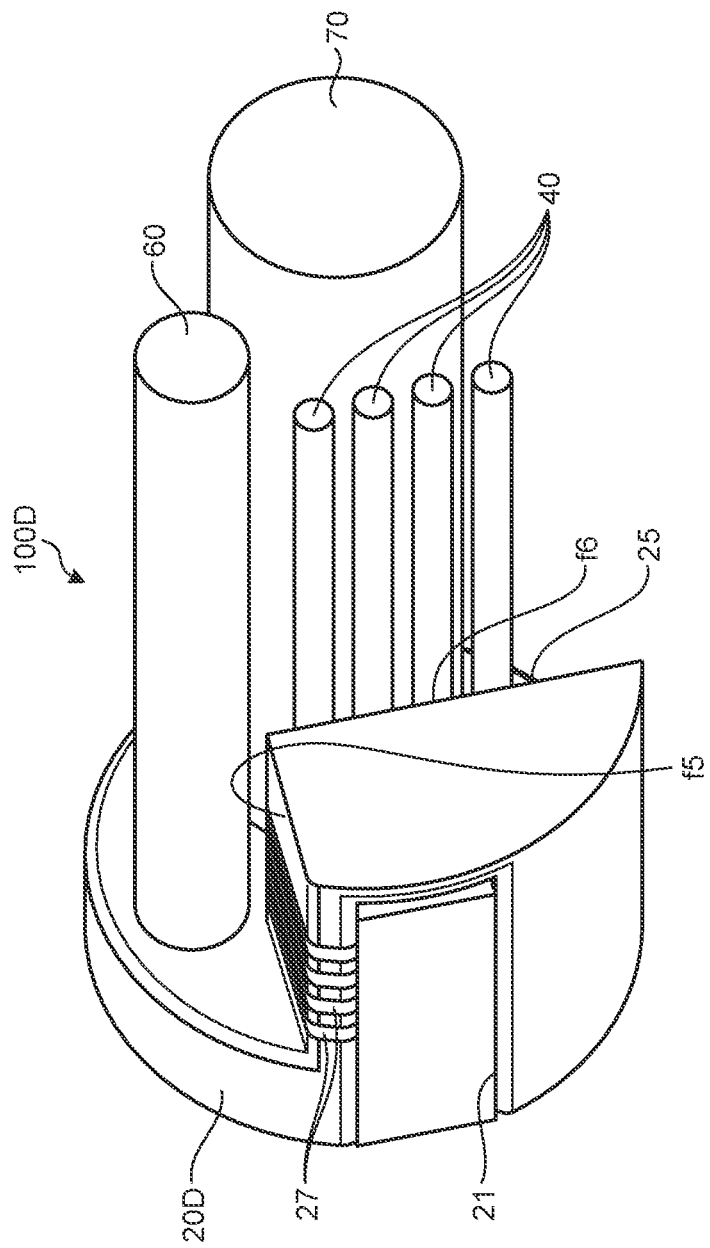
FIG. 17 is a perspective view of the endoscope distal end structure of FIG. 16 from another direction.

In a fifth embodiment, periphery of a channel 70 and a light guide 60 is cut out on the proximal end side of a distal end frame 20D, and a cable connection portion 25D is disposed in the vicinity of the center of the distal end frame 20G. FIG. 16 is a perspective view of an endoscope distal end structure 100D according to the fifth embodiment, and FIG. 17 is a perspective view of the endoscope distal end structure 100D of FIG. 16 from another direction. In FIGS. 16 and 17, illustration of the outer frame is omitted.

The distal end frame 20D includes a first body portion 20D-1 having a columnar shape on the distal end side, and a second body portion 20D-2 in which the housing portion 21 of the imaging unit 30 is formed together with the first body portion 20D-1. The periphery of the channel 70 and the light guide 60 is cut out on the proximal end side of the distal end frame 20D except for the second body portion 20D-2.

In the endoscope, an observation direction is defined by operating a bendable bending portion 6b including a number of bending pieces by an angle wire (not illustrated). Two angle wires in the upper and lower directions or four angle wires in the upper, lower, left, and right directions (not illustrated) are inserted in the vicinity of the bending pieces of the insertion portion, that is, in an outer peripheral side of the insertion portion depending on the type of the endoscope. When the cable connection portion is provided on the outer peripheral side of the distal end frame, the signal cable 40 and the angle wire (not illustrated) may interfere with each other. Therefore, in the fifth embodiment, the periphery of the channel 70 and the light guide 60 on the proximal end side of the distal end frame 20D is cut out, and the cable connection portion 25D is disposed on a center side of the distal end frame 20D to prevent interference with the angle wire (not illustrated).

The cable connection portion 25D includes the plane f5 and the plane f6. The cable connection electrode is disposed on the plane f6.

The wiring pattern 27 connects the connection terminal and the cable connection electrode, and is formed in a housing portion 21D, a part of the outer periphery of distal end frame 20D, and the cable connection portion 25D.

In the endoscope distal end structure 100D, when viewed in the front-rear direction with reference to the optical axis O direction of the imaging unit 30, the cable connection electrode connecting the core wire 41 of the signal cable 40 is formed on the distal end side from the bottom surface of the housing portion 21D. By forming the cable connection electrode on the distal end side from the bottom surface f1 of the housing portion 21D, the length r1 of the distal end frame 20D in the optical axis O direction may be reduced.

In addition, the corners of the housing portion 21D in which the wiring pattern 27 is formed, of a part of the outer periphery (side surface) of the distal end frame 20D, and of the cable connection portion 25D, that is, the corner between the bottom surface f1 and the side surface f2 of the housing portion 21D, the corner between the side surface f2 and the side surface f3, the corner between the side surface f3 and the outer periphery (side surface) of the distal end frame 20D, the corner between the outer periphery (side surface)

of the distal end frame 20D and the cable connection portion 25D, and the corner between the plane f5 and the plane f6 have a chamfer 33. By chamfering the corners, it is possible to prevent degradation of quality of electric signals transmitted through the wiring pattern 27.

Sixth Embodiment

Figure 18:
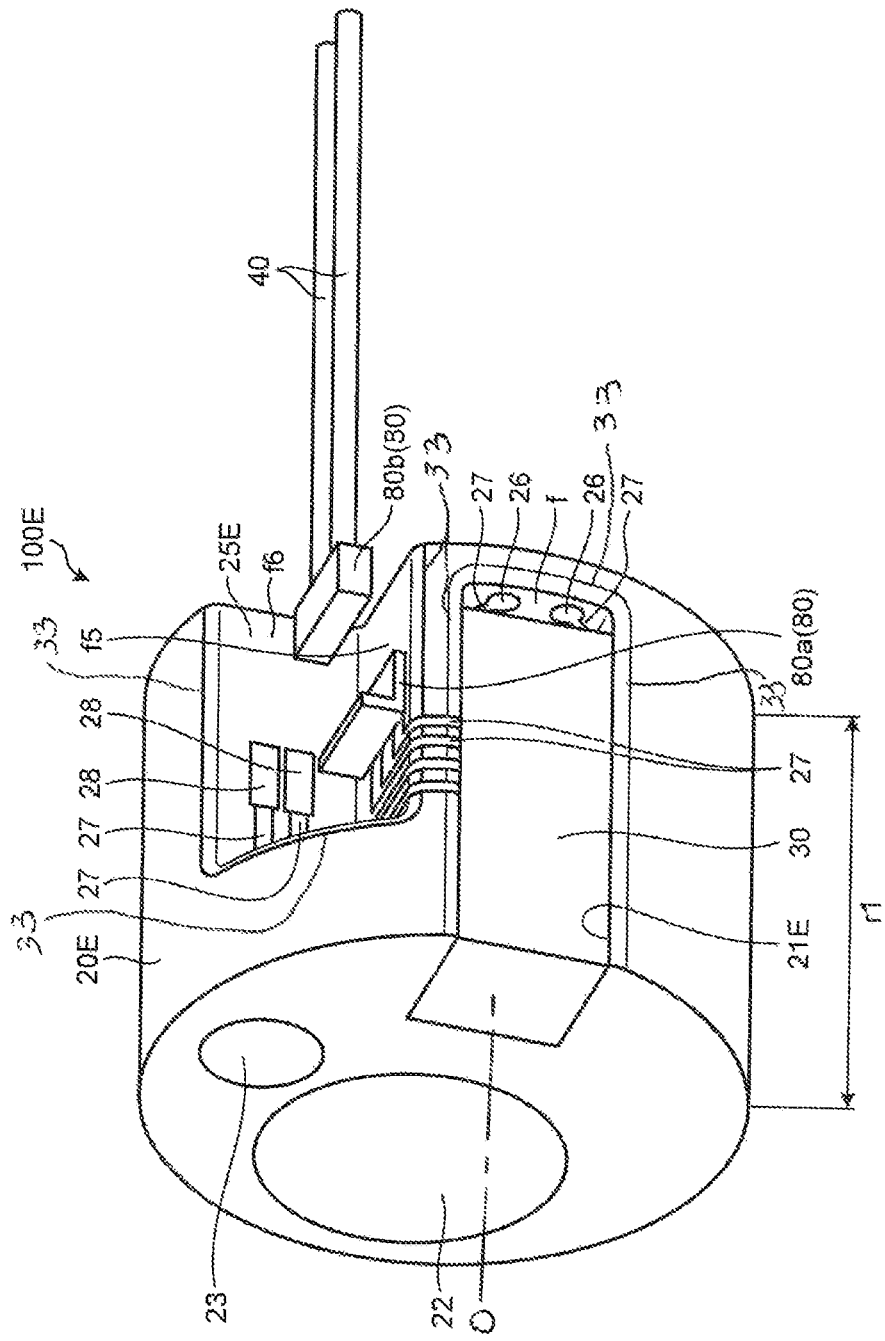
FIG. 18 is a perspective view of the endoscope distal end structure according to a sixth embodiment.

In a sixth embodiment, the signal cable 40 is connected to a cable connection portion 25B via a connector 80. FIG. 18 is a perspective view of an endoscope distal end structure 100E according to the sixth embodiment. FIG. 18 is a view before the signal cable 40 is attached to the cable connection portion 25E, and the illustration of the light guide and the channel is omitted.

The cable connection portion 25E includes planes f5 and f6, and a receiving connector 80a is disposed on the wiring pattern 27 of the plane f5.

A distal end side of the signal cable 40 from which the core wire is exposed is attached to a connector 80b. By fitting the connector 80b to the receiving connector 80a, the core wire of the signal cable 40 and the connection land of the imaging unit 30 are electrically connected by the wiring pattern 27, the connection terminal, and the bump in FIG. 18, the signal cable 40 is not connected to the cable connection electrode 28 of the plane f6, but the core wire of the signal cable 40 may be directly connected or may be connected via the connector 80.

Since the receiving connector 80a may be connected to the distal end frame 20E by reflow, the signal cable 40 may be easily attached to the distal end frame 20E. In addition, in general, after the imaging unit 30 is attached to the distal end frame 20E, the signal cable 40 is connected to the distal end frame 20E, but by connecting the receiving connector 80a before the imaging unit 30 is attached, thermal history applied to the imaging unit may be reduced.

Further, similarly to the first and second embodiments, when viewed in the front-rear direction with reference to the optical axis O direction of the imaging unit 30, the receiving connector 80a to which the signal cable 40 is connected is formed on the distal end side from the bottom surface f1 of the housing portion 21, so that the length r1 of the distal end frame 20 in the optical axis O direction may be reduced.

In addition, the corners of the housing portion 21E in which the wiring pattern 27 is formed, of a part of the outer periphery (side surface) of the distal end frame 20E, and of the cable connection portion 25E, that is, the corner between the bottom surface f1 and the side surface f2 of the housing portion 21E, the corner between the side surface f2 and the side surface f3, the corner between the side surface f3 and the outer periphery (side surface) of the distal end frame 20E, the corner between the outer periphery (side surface) of the distal end frame 20E and the plane f5 of the cable connection portion 25E, and the corner between the plane f5 and the plane f6 have a chamfer 33. By chamfering the corners, it is possible to prevent degradation of quality of electric signals transmitted through the wiring pattern 27.

The endoscope distal end structure and the endoscope are useful for the endoscope system that requires smaller diameter and shorter length.

According to the present disclosure, it is possible to reduce a diameter and a length of the distal end portion of the endoscope.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope distal end structure comprising:
    an imaging unit comprising an image sensor configured to capture an image of a subject;
    a plurality of signal cables configured to transmit and receive a signal to and from the imaging unit; and
    a distal end frame that is a three-dimensional circuit component, the distal end frame comprising:
        a housing portion being recessed from an outer periphery and from a distal end face of the distal end frame, the housing portion being configured to house the imaging unit, and
        a cable connection portion configured to connect the plurality of signal cables, wherein
    the housing portion includes a proximal surface offset from the distal end face in an optical axis direction of the imaging unit and a side surface offset from the proximal surface, and the proximal surface is provided with a plurality of imaging unit connection terminals respectively corresponding to the plurality of signal cables for electrically connecting the imaging unit,
    the cable connection portion is provided with a plurality of cable connection electrodes respectively corresponding to the plurality of imaging unit connection terminals, each cable connection electrode of the plurality of cable connection electrodes connecting a core wire of each respective signal cable of the plurality of signal cables, all portions of the plurality of cable connection electrodes are distal to the proximal surface of the housing portion in the optical axis direction of the imaging unit, and
    the plurality of imaging unit connection terminals and the plurality of cable connection electrodes are respectively connected by a wiring pattern formed in the housing portion, on an outer periphery of the distal end frame, and in the cable connection portion.

2. The endoscope distal end structure according to claim 1, wherein the imaging unit and the plurality of signal cables are located in a projection plane of a circumscribed circle of a circumferential surface in an optical axis direction of the distal end frame.

3. The endoscope distal end structure according to claim 1, wherein the plurality of imaging unit connection terminals include at least a power terminal required to drive the imaging unit, a ground terminal, and a video signal terminal.

4. The endoscope distal end structure according to claim 1, wherein the cable connection portion includes one or more planes, and the plurality of cable connection electrodes are formed on each of the one or more planes.

5. The endoscope distal end structure according to claim 4, wherein the a distance between the one or more planes and a central axis of the distal end frame is stepwise reduced in a proximal direction.

6. The endoscope distal end structure according to claim 1, wherein the cable connection portion includes a circumferential surface concentric with the outer periphery of the distal end frame.

7. The endoscope distal end structure according to claim 6, wherein a diameter of the circumferential surface is stepwise reduced in a proximal direction.

8. The endoscope distal end structure according to claim 1, wherein the distal end frame has a channel insertion hole configured to accommodate a channel tube therein and a light guide insertion hole configured to accommodate a light guide therein, and the cable connection portion comprises a first cable connection portion and a second cable connection portion, a central axis of the channel insertion hole and an optical axis of the imaging unit being between the first cable connection portion and the second cable connection portion in a cross-section of the distal end frame taken perpendicular to the optical axis direction.

9. The endoscope distal end structure according to claim 1, wherein housing portion has a plurality of corners over which the wiring pattern extends, and the plurality of corners are chamfered.

10. The endoscope distal end structure according to claim 1, wherein a connector is connected to the plurality of cable connection electrodes.

11. An endoscope comprising the endoscope distal end structure according to claim 1.

\* \* \* \* \*